United States Patent

Noack et al.

Patent Number: 5,463,114
Date of Patent: Oct. 31, 1995

[54] PROCESS FOR THE PRODUCTION OF ETHER CARBOXYLIC ACIDS AND SALTS THEREOF

[75] Inventors: Wolf-Eckart Noack, Essen; Paul Schulz, Wuppertal, both of Germany; F. Norman Tuller, Simpsonville, S.C.

[73] Assignee: Henkel Kommanditgesellschaft auf Aktien, Duesseldorf, Germany

[21] Appl. No.: 226,903

[22] Filed: Apr. 13, 1994

[51] Int. Cl.$^6$ .................................. C07C 51/235
[52] U.S. Cl. ............................ 562/421; 562/539
[58] Field of Search ...................... 562/421, 539

[56] References Cited

U.S. PATENT DOCUMENTS

| | | | |
|---|---|---|---|
| 4,214,101 | 7/1980 | Miya et al. | 562/421 |
| 4,607,121 | 8/1986 | Faggian et al. | 562/537 |
| 5,292,940 | 3/1994 | Noack et al. | 562/538 |

FOREIGN PATENT DOCUMENTS

| | | |
|---|---|---|
| 0073545 | 3/1983 | European Pat. Off. . |
| 2816127 | 11/1978 | Germany . |
| 3446561 | 7/1985 | Germany . |
| 3929063 | 3/1991 | Germany . |

*Primary Examiner*—José G. Dees
*Assistant Examiner*—Barbara S. Frazier
*Attorney, Agent, or Firm*—Wayne C. Jaeschke; John E. Drach; Henry E. Millson, Jr.

[57] ABSTRACT

Ether carboxylic acids of the formula (I):

$$R-(OC_mH_{2m})_n-O-CH_2COOM \qquad (I)$$

wherein R is an alkyl group having from 1 to about 22 carbon atoms, an aryl group or an aralkyl group; m is 2 or 3; n is a number from 1 to about 200; M is an alkali metal are made by oxidation of an ether alcohol wherein the ether alcohol, oxygen, and an alkali metal hydroxide are continuously added to an aqueous dispersion of a noble metal catalyst under reduced pressure.

17 Claims, No Drawings

PROCESS FOR THE PRODUCTION OF ETHER CARBOXYLIC ACIDS AND SALTS THEREOF

BACKGROUND OF THE INVENTION

1. Field of the Invention

This invention relates to a process for the production of ether carboxylic acid salts by oxidation of ether alcohols with oxygen in the presence of a catalyst.

2. Description of the Related Art

The production of ether carboxylic acids and salts thereof is described in a number of publications. For example, U.S. Pat. No. 4,214,101 describes a process for the production of ether carboxylic acids in which fatty alcohol polyglycol ethers are contacted while stirring with oxygen in the presence of a palladium catalyst at a pH value of 8 to 13 and at a temperature of 50° to 95° C. On completion of the reaction, the catalyst is filtered off and the free ether carboxylic acid is released from the alkali metal salt by acidification.

Patent applications DE-A 28 16 127, DE-A 34 46 561 and EP-A 0 073 545 describe similar processes, namely oxidation with pure oxygen under slight excess pressures (above atmospheric pressure) and with catalysts, such as Pd/C, Pt/C, or mixed catalysts, such as Pd/Pt/C, the reaction being carried out at a pH value of 8 to 13.

One feature common to the processes described in the documents mentioned above is that the entire ether alcohol is introduced at the beginning of the reaction and the oxidation is carried out under oxygen partial pressures slightly above atmospheric pressure ($P_{O_2}$ approximately 1 bar abs.).

As described in DE-A 28 16 127, it was found when carrying out the reaction that the viscosity of the reaction solution initially increases with increasing conversion, reaching a maximum at a conversion of 20 to 30% and then falling drastically as the reaction progresses. In tests carried out by applicants, it was found that the level of the viscosity maximum increases with increasing concentration of the ether alcohol used, with increasing C chain length and with a decreasing number of ethylene oxide groups. The effect of the viscosity maximum is that the reaction takes place more slowly and, in the most unfavorable case, actually comes to a stop. For example, it is almost impossible to oxidize a 20% aqueous $C_{12/14}$ 4EO ethoxyalcohol solution to form the corresponding ether carboxylic acid. In this case, viscosity increases to such an extent that the reaction comes to a stop. On the other hand, a $C_{12/14}$ 11EO ethoxyalcohol of the same concentration can be oxidized without problems. For the reasons mentioned above, however, it is not possible to react an only 10% aqueous $C_{16/18}$ 6EO ethoxyalcohol solution.

DE-A 39 29 063 describes a process in which the viscosity can be kept below the maximum by introduction of the ether alcohol during the reaction in dependence upon its consumption. A solution with a high concentration of reacted ether alcohol can thus be obtained on completion of the reaction. Through addition of the ether alcohol at a rate commensurate with that at which it reacts off, the concentration of unreacted ether alcohol in the reaction solution can be kept substantially constant throughout the reaction.

In the process described in DE-A 39 29 063 the oxidation is not carried out with pure oxygen, but instead with air. This inevitably results in a waste gas stream. On account of the intensive foaming of the starting materials and end products, foam is discharged with the waste gas. To suppress foaming and hence the discharge of reaction solution, special equipment-related measures have to be taken, for example by the provision of a co-current column with a suspension circuit such as described in DE-A 39 29 063. A disadvantage of oxidation with air is that the waste gas stream entrains ether alcohol in accordance with its vapor pressure and thus causes a certain degree of environmental pollution.

A disadvantage of carrying out the process under oxygen pressures above atmospheric pressure as described in the prior art is that the catalyst can be deactivated by an oversupply of oxygen. Tests have shown that, in particular, a repeatedly used catalyst is prematurely deactivated where the reaction is carried out under high oxygen pressures so that only an incomplete conversion is obtained.

The problem addressed by the present invention was to provide an industrial-scale process for the production of ether carboxylic acids by oxidation of ether alcohols with oxygen, in which ethoxyalcohols with any ethylene oxide contents and any carbon chain lengths could be oxidized in high conversions by continuous introduction of ether alcohol to form the corresponding ether carboxylic acids or alkali metal salts thereof in the form of highly concentrated solutions, the reaction being carried out without any waste gas using an already repeatedly used catalyst.

SUMMARY OF THE INVENTION

The present invention relates to a process for the production of ether carboxylic acids or salts thereof corresponding to formula (I):

$$R-(OC_mH_{2m})_n-O-CH_2COOM \qquad (I)$$

wherein R is an alkyl group having from 1 to about 22 carbon atoms, an aryl group or an aralkyl group; m is 2 or 3; n is a number from 1 to about 200; M is an alkali metal; which comprises the steps of: (1) providing a mixture comprised of water and a noble metal catalyst; reducing the pressure above said mixture to a value of from about 0.01 to about 0.1 bar; (2) heating said mixture to a temperature of from about 50° C. to about 130° C.; (3) simultaneously adding to said mixture the following substances: (a) an ether alcohol of the formula (II)

$$R-(OC_mH_{2m})_n-O-CH_2CH_2OH \qquad (II)$$

wherein R, m, and n are defined as above at a rate sufficient to maintain the quantity of unreacted ether alcohol at from about 0.1% to about 15% by weight; (b) an aqueous alkali metal hydroxide solution at a rate sufficient to maintain the pH at a value of at least 8; (c) oxygen at a rate sufficient to maintain the partial oxygen pressure in the range of from about 0.1 bar to 0.3 bar.

DESCRIPTION OF THE PREFERRED EMBODIMENTS

Other than in the claims and in the operating examples, or where otherwise indicated, all numbers expressing quantities of ingredients or reaction conditions used herein are to be understood as modified in all instances by the term "about".

It has surprisingly been found that ether carboxylates can be obtained in high yields from the corresponding ether alcohols by the process according to the invention irrespective of their carbon chain length and their degree of alkoxylation and in that the reaction can be carried out with an already repeatedly used catalyst.

Suitable starting compounds corresponding to formula II are ether alcohols in which the substituent R is a linear or branched $C_{1-22}$ alkyl group. Typical examples of R are methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, uneicosyl and dosocyl. The process according to the invention is particularly suitable for the production of ether carboxylic acids or salts thereof when the substituent R is derived from $C_{8-18}$ fatty alcohols or technical mixtures thereof obtainable from animal and/or vegetable fats and oils. The substituent R may also be an aryl radical, for example a phenyl alkylene group containing 1 to 3 carbon atoms in the alkylene radical.

The compound corresponding to general formula II is an adduct of ethylene oxide or ethylene oxide and propylene oxide with alcohols corresponding to the formula ROH. In the case of the ethylene oxide/propylene oxide adducts corresponding to formula II, the propylene glycol groups may be present in random or block distribution in the alkoxylate chain, although a terminal ethylene glycol group is always present. n is preferably a number of 1 to 20. Adducts of ethylene oxide with alcohols corresponding to the formula ROH are preferred for the purposes of the invention, so that m is preferably 2 for the compounds corresponding to formulae I and II.

The process according to the invention is carried out in the presence of a catalyst. Known noble metal catalysts, more particularly those based on platinum or palladium, are suitable. Palladium catalysts, for example palladium on carbon, have proved to be particularly suitable for the process according to the invention. In addition, the catalysts may contain combinations of several noble metals instead of a single noble metal, for example mixtures of palladium and platinum, and other activators, such as lead, bismuth or cadmium in the form of their metals or their compounds, including mixtures thereof. The catalyst contains 1 to 10% by weight of active substance, based on the total weight of the catalyst. Suitable catalysts are described, for example, in U.S. Pat. No. 4,607,121. The catalyst is preferably present in a quantity of 0.2 to 10% by weight and more preferably in a quantity of 0.2 to 3% by weight, based on the reaction mixture as a whole.

According to the invention, the reactor initially filled with catalyst and water is evacuated to a pressure of 0.01 to 0.1 bar before the heating phase. This ensures that the addition of ether alcohol and NaOH during the reaction does not compress the nitrogen present in the closed reactor which would normally result in an unwanted increase in pressure.

After evacuation, the reaction mixture is heated to a temperature of 50° to 130° C. and preferably to a temperature of 60° to 95° C. In one preferred embodiment, the ether alcohol corresponding to formula II is only added to the evacuated reactor during the heating phase. To avoid the increase in viscosity occurring at relatively high ether alcohol concentrations, the ether alcohol is initially introduced in accordance with the invention in a concentration of 0.1 to 15% by weight and preferably in a concentration of at least 0.5 to 7% by weight, based on the total weight of the reaction mixture.

When the reaction temperature has been reached, oxygen is introduced into the suspension accommodated in the reactor. The oxygen is preferably introduced below the stirrer. The process according to the invention is carried out with oxygen gas which is added at such a rate—in dependence upon its consumption—that the oxygen partial pressure remains substantially constant. During the reaction, the oxygen partial pressure is adjusted to a value of 0.1 to 0.6 bar and preferably to a value of 0.1 to 0.3 bar. The oxygen gas should contain at least 98% of oxygen and preferably at least 99.8%. Oxygen partial pressures of more than 0.6 bar should be avoided because, if it has already been used several times, the catalyst would otherwise be deactivated.

During the reaction, the ether alcohol corresponding to formula II is introduced into the reaction solution continuously or in portions in such a quantity that the ether alcohol is present in the reaction mixture in a concentration of 0.1 to 15% by weight and preferably in a concentration of at least 0.5 to 7% by weight, based on the total weight of the reaction mixture.

It has surprisingly been found that, where the reaction is carried out in accordance with the invention, i.e. without an inert gas, the catalyst used shows greater activity than where the reaction is carried out in the presence of nitrogen (see FIG. 1). Where the reaction is carried out with an inert gas, the oxygen partial pressure at the point of introduction of the oxygen is very high on account of the above-mentioned compression of the inert gas, particularly towards the end of the reaction. Taking into account the test results obtained in connection with the present invention, it is assumed that this increased oxygen partial pressure leads to deactivation of the catalyst. However, if the reactor is evacuated at the beginning, as in the process according to the invention, the total reactor pressure during the reaction is lower because there is no inert gas to be compressed. Accordingly, the oxygen can be introduced under a relatively low pressure, resulting in relatively low oxygen partial pressures at the point where the oxygen is introduced. The increased catalyst activity in the process according to the invention is reflected in an increased reaction rate and in a higher conversion by comparison with the case where the process is carried out with an inert gas at the same temperature (see Example).

The process according to the invention is carried out at pH values of at least 8. pH values of at least 9 are particularly advantageous, pH values in the range from 9 to 12.5 being particularly preferred. The pH value is preferably kept substantially constant during the reaction by continuous neutralization of the acid formed by addition of alkali metal hydroxide, such as NaOH, KOH or LiOH.

On completion of the reaction, the suspension is filtered. The reaction product obtained in the form of the acid salt may be converted into the free acid by acidification of the filtrate with an acid to a pH value at the equivalence point. The acids used are mineral acids, $H_2SO_4$ and $H_3PO_4$. HCl is preferably used. The ether carboxylic acid released is then isolated in known manner.

The process according to the invention may be carried out in standard reactors which provide for adequate gas/liquid contact. A stirred reactor is preferably used.

The following Examples are intended to illustrate the invention without limiting it in any way.

EXAMPLE

In this Example, the process according to the invention is carried out on a pilot-plant scale.
Equipment
  a) Stirred tank reactor: capacity 330 l, internal diameter 0.7 m
  b) Stirrer: 3-stage Intermig, diameter 0.43 m
  c) $O_2$ introduction: below the stirrer Starting compound $C_{12/14}$ ether alcohol - 6 EO (MW: 460, OH value 122)

Test procedure

1. The stirred tank reactor is filled with a suspension consisting of 4 kg of catalyst (5% Pd/C, E 101 R/W, a product of Degussa AG), expressed as solids, 230 l of demineralized water and 0.5 kg of NaOH solution (25%) and subsequently evacuated to a pressure of approximately 40 mbar.

2. After application of the vacuum, the reactor is closed and the suspension is heated with stirring to 80° C. The reactor pressure is then around 0.5 bar abs. corresponding to the water vapor pressure. During the heating phase, 6 kg of ether alcohol are introduced and the alcoholic suspension is stirred for 20 minutes at 80° C.

3. The stirrer is then adjusted to a rotational speed of 220 r.p.m. and oxygen is slowly introduced into the stirred tank so that the reactor pressure increases by 0.1 to 0.2 bar. The onset of the reaction is reflected in the uptake of oxygen with no change in pressure and a fall in the pH value.

4. During the reaction, NaOH solution is added in such a quantity that the pH value remains between 10.2 and 10.5. The corresponding conversion of ether alcohol to ether carboxylic acid is calculated from the NaOH solution removed and ether alcohol is introduced into the reaction solution in such a quantity that the quantity of unreacted alcohol is between 5 and 7 kg. The reactor pressure $P_{total}$ is adjusted at the point of introduction of the oxygen in such a way that $$P_{total} - P_{H2O} - P_{stat} = P_{O2} = 0.1 - 0.2 \text{ bar,}$$

$P_{total}$ being the total reactor pressure at the oxygen inlet, $P_{H2O}$ being the water vapor pressure at the particular temperature and $P_{stat}$ being the hydrostatic pressure of the liquid column above the oxygen inlet.

5. After 55 kg of ether alcohol have been introduced, the reaction is continued until the remaining ether alcohol has been largely consumed. This is reflected in the absence of any further uptake of NaOH and oxygen. Filtration of the suspension leaves a clear approximately 20% aqueous sodium salt solution of the ether carboxylic acid C12/C14-5EO.

6. The filtrate is acidified with $H_2SO_4$ to a pH value of 2.7 and heated to 90° C. so that phase separation begins. The organic phase is subsequently dried and filtered. The clear, pale yellow ether carboxylic acid thus obtained as the following characteristics: acid value 110, saponification value 111, OH value 5.0. This gives a conversion of approximately 95%.

FIG. 1 shows the conversion of the reaction as a function time for case A (reaction carried out in the presence of an inert gas) and for case B (reaction carried out in the absence of an inert gas) at 81° C. under an average oxygen partial pressure of 0.3 bar.

| Stage of the reaction | Curve A: With inert gas | | Curve B: Without inert gas | |
|---|---|---|---|---|
| | Start | End | Start | End |
| $P_{H2O}$ (bar) | 0.5 | 0.5 | 0.5 | 0.5 |
| $P_{N2}$ (bar) | 0.5 | 1.5 | 0 | 0 |
| $P_{O2}$ (bar) | 0.3 | 0.3 | 0.3 | 0.3 |
| $P_{total}$ (bar) | 1.3 | 2.3 | 0.8 | 0.8 |

$P_{total} = P_{H2O} + P_{N2} + P_{O2}$ = total pressure = oxygen pressure at the $O_2$ inlet -continued

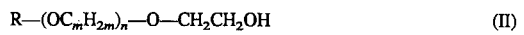

| Stage of the reaction | Curve A: With inert gas | | Curve B: Without inert gas | |
|---|---|---|---|---|
| | Start | End | Start | End |

$P_{O2}$ = spatially averaged oxygen partial pressure
The hydrostatic pressure was disregarded.

It can be seen from the Figure that carrying out the reaction in accordance with the invention in the absence of an inert gas leads to distinctly higher reaction rates. In case A, the reaction had to be prematurely terminated on account of an excessively low reaction rate.

What is claimed is:

1. A process for making an ether carboxylic acid salt corresponding to formula (I):

$$R-(OC_mH_{2m})_n-O-CH_2COOM \qquad (I)$$

wherein R is an alkyl group having from 1 to 22 carbon atoms, an aryl group or an aralkyl group; n is 2 or 3; n is a number from 1 to 200; M is an alkali metal; which comprises the steps of: (1) providing a mixture comprised of water and a noble metal catalyst; evacuating to a pressure above said mixture of from about 0.01 to about 0.1 bar; (2) heating said mixture to a temperature of from about 50° C. to about 130° C.; (3) simultaneously adding to said mixture the following: (a) an ether alcohol of the formula (II)

$$R-(OC_mH_{2m})_n-O-CH_2CH_2OH \qquad (II)$$

wherein R, m, and n are defined as above at a rate sufficient to maintain the quantity of unreacted ether alcohol at from about 0.1% to about 15% by weight; (b) an aqueous alkali metal hydroxide solution at a rate sufficient to maintain the pH at a value of at least 8; (c) oxygen at a rate sufficient to maintain the partial oxygen pressure in the range of from about 0.1 bar to about 0.6 bar; wherein the ether alcohol of formula II is not present in the mixture in step (1).

2. The process of claim 1 wherein said noble metal catalyst is palladium on carbon.

3. The process of claim 1 wherein said alkali metal hydroxide is LiOH, NaOH, or KOH.

4. The process of claim 1 wherein said pH is maintained at a value of from about 9 to about 12.5.

5. The process of claim 1 wherein in said compound of formula (I), R is a $C_{8-18}$ alkyl group, m is 2 and n is a number from 1 to 20.

6. The process of claim 1 wherein in step (3)(c) the partial oxygen pressure is maintained in the range of from about 0.1 bar to about 0.3 bar.

7. The process of claim 1 wherein the noble metal catalyst is a platinum or palladium catalyst or a mixture thereof.

8. The process of claim 7 wherein the catalyst contains from about 1 to about 10% by weight of active substance.

9. The process of claim 1 wherein in the process the catalyst is present in a quantity of from about 0.2 to about 10% by weight, based on the total weight of the reaction mixture.

10. The process of claim 9 wherein said quantity is from about 0.2 to about 3% by weight.

11. The process of claim 1 wherein step (2) is carried out at a temperature in the range of from 60° to about 95° C.

12. The process of claim 1 wherein in step (3)(a) the ether alcohol of formula II is added at a rate sufficient to maintain the quantity of unreacted ether alcohol at from about 0.5% to about 7% by weight.

13. The process of claim 1 wherein in step (3)(c) the oxygen contains at least 98% pure oxygen.

14. The process of claim 13 wherein the oxygen contains at least 99.8% pure oxygen.

15. The process of claim 1 wherein in said compound of formula I, R is a $C_{8-18}$ alkyl group, m is 2 and n is a number from 1 to 20; in step (3)(c) the partial oxygen pressure is maintained in the range of from about 0.1 bar to about 0.3 bar; and in step (2) the temperature is in the range of from about 60° to about 95° C.

16. The process of claim 15 wherein in step (1) the noble metal catalyst is a platinum or palladium catalyst or a mixture thereof; in step (3)(a) the ether alcohol of formula T is added at a rate sufficient to maintain the quantity of unreacted ether alcohol at from about 0.5% to about 7% by weight; and in step (3)(b) the alkali metal hydroxide is LiOH, NaOH, or KOH.

17. The process of claim 16 wherein the noble metal catalyst is palladium on carbon.

* * * * *